United States Patent
Rhodes (10) Patent No.: US 6,830,730 B2
(45) Date of Patent: Dec. 14, 2004

(54) METHOD AND APPARATUS FOR THE ON-STREAM ANALYSIS OF TOTAL SULFUR AND/OR NITROGEN IN PETROLEUM PRODUCTS

(75) Inventor: John R. Rhodes, Austin, TX (US)

(73) Assignee: SpectrolAnalytical Instruments, Marble Falls, TX (US)

( * ) Notice: Subject to any disclaimer, the term of this patent is extended or adjusted under 35 U.S.C. 154(b) by 86 days.

(21) Appl. No.: 09/951,760

(22) Filed: Sep. 11, 2001

(65) Prior Publication Data
US 2003/0049854 A1 Mar. 13, 2003

(51) Int. Cl.[7] ............................................. G01N 31/12
(52) U.S. Cl. ............................. 422/78; 422/50; 422/62; 422/82.01; 422/82.02; 422/83; 422/90
(58) Field of Search .............................. 422/50, 62, 78, 422/82.01, 82.02, 83, 90, 91

(56) References Cited

U.S. PATENT DOCUMENTS

| | | | |
|---|---|---|---|
| 3,622,488 A | | 11/1971 | Chand et al. ............... 204/195 |
| 3,650,696 A | | 3/1972 | Eads .......................... 23/230 |
| 3,683,669 A | * | 8/1972 | Kraus ........................ 73/19.12 |
| 3,795,812 A | | 3/1974 | Okabe ........................ 250/373 |
| 3,835,322 A | * | 9/1974 | Komatsu ..................... 436/118 |
| 3,838,969 A | | 10/1974 | Dugan ......................... 23/230 |
| 3,840,341 A | * | 10/1974 | Rogers ........................ 436/146 |
| 3,854,881 A | * | 12/1974 | Cohen ......................... 422/79 |
| 3,894,419 A | | 7/1975 | Mator et al. ................... 73/1 |
| 3,925,332 A | | 12/1975 | Naito et al. ................. 260/79.3 |
| 3,976,450 A | | 8/1976 | Marcote et al. ............... 55/158 |
| 4,004,882 A | | 1/1977 | Byrne et al. .................. 23/254 |
| 4,018,562 A | | 4/1977 | Parks et al. ................... 23/230 |
| 4,066,409 A | | 1/1978 | Fine ............................ 23/230 |
| 4,070,155 A | | 1/1978 | Fraim ........................... 23/230 |
| 4,073,304 A | * | 2/1978 | Lerner et al. .......... 137/101.21 |

(List continued on next page.)

FOREIGN PATENT DOCUMENTS

| | | | | |
|---|---|---|---|---|
| EP | 0127387 A2 | 12/1984 | | |
| GB | 2017315 | 10/1979 | | |
| GB | 1578281 | 11/1980 | | |
| GB | 2049952 | 12/1980 | | |
| GB | 2319606 | 5/1998 | | |
| GB | 2323171 | 9/1998 | | |
| JP | 2001232137 A | * 8/2001 | ........... | B01D/53/26 |
| WO | WO 8707721 A | * 12/1987 | .......... | G01N/21/64 |
| WO | WO 94/07134 | 3/1994 | | |
| WO | WO 95/22049 | 8/1995 | | |
| WO | WO 99/18430 | 4/1999 | | |
| WO | WO 99/58950 | 11/1999 | | |
| WO | WO 01/46683 A2 | 6/2001 | | |

OTHER PUBLICATIONS

Manual MAN–0027–00 "SO2 detector" Net Safety Monitoring, Inc. 2000 http://www.net–safety.com/PDF/Toxic%20Gas/Manuals/MAN–0027–00.pdf.*

(List continued on next page.)

Primary Examiner—Yelena G. Gakh
(74) Attorney, Agent, or Firm—Vinson & Elkins L.L.P.

(57) ABSTRACT

An improved on-stream analyzer for monitoring sulfur or nitrogen content of liquid petroleum or beverage products is described. It consists of the following main components: a sample injector for injecting predetermined fixed volumes of the liquid into a thermal oxidizer (pyrolyzer) at a preset, controlled rate, a thermal oxidizer in which an inert carrier gas and oxygen are introduced at measured and preset, controlled rates to thermally oxidize the sample at a temperature of about 1050° C., sample conditioner to control the relative humidity and temperature of the resulting gas mixture, an electrochemical cell sensitive to sulfur dioxide ($SO_2$) or NO to measure the concentration of $SO_2$ or NO in the gas mixture, and a programmable logic controller (PLC) to calculate the sulfur content of the original sample and manage the analyzer. Although the analyzer is designed primarily for monitoring sulfur content of petroleum and beverage products, it is recognized that essentially the same equipment can be used to analyze any liquid having a suitable viscosity and capable of being completely thermally oxidized under the conditions specified.

44 Claims, 4 Drawing Sheets

U.S. PATENT DOCUMENTS

| | | | |
|---|---|---|---|
| 4,077,774 A | | 3/1978 | Neti et al. .................... 23/232 |
| 4,147,500 A | * | 4/1979 | Karlsoen ................. 73/863.12 |
| 4,172,705 A | | 10/1979 | Castro et al. ................. 23/230 |
| 4,223,324 A | | 9/1980 | Yamamori et al. .......... 346/140 |
| 4,257,772 A | | 3/1981 | Bognin et al. ................ 23/230 |
| 4,257,777 A | | 3/1981 | Dymond et al. ............. 23/232 |
| 4,271,697 A | * | 6/1981 | Mowery, Jr. ............... 73/61.52 |
| 4,272,248 A | | 6/1981 | Neti ............................ 23/232 |
| 4,275,752 A | * | 6/1981 | Collier et al. .................. 137/7 |
| 4,293,308 A | | 10/1981 | Sisti et al. .................... 23/230 |
| 4,296,637 A | * | 10/1981 | Calamur et al. ......... 73/863.11 |
| 4,301,114 A | | 11/1981 | Rounbehler et al. .......... 422/52 |
| 4,330,298 A | | 5/1982 | Hawn et al. .................. 23/230 |
| 4,332,591 A | | 6/1982 | Oi et al. ....................... 23/230 |
| 4,351,801 A | | 9/1982 | Bartke .......................... 422/78 |
| 4,352,779 A | | 10/1982 | Parks ........................... 422/52 |
| 4,372,915 A | * | 2/1983 | Neti et al. .................... 422/91 |
| 4,401,763 A | | 8/1983 | Itoh ........................... 436/115 |
| 4,409,336 A | | 10/1983 | Oita ........................... 436/123 |
| 4,467,038 A | | 8/1984 | Scott .......................... 436/115 |
| 4,587,003 A | | 5/1986 | Tantram et al. ............. 204/412 |
| 4,633,021 A | | 12/1986 | Hanes ........................ 568/454 |
| 4,633,704 A | | 1/1987 | Tantram et al. ................. 73/23 |
| 4,678,756 A | | 7/1987 | Parks ......................... 436/123 |
| 4,765,961 A | | 8/1988 | Schiff et al. .................. 422/52 |
| 4,766,760 A | | 8/1988 | Poshemansky et al. ...... 73/23.1 |
| 4,778,764 A | | 10/1988 | Fine ........................... 436/116 |
| 4,843,016 A | | 6/1989 | Fine ........................... 436/106 |
| 5,042,500 A | * | 8/1991 | Norlien et al. .............. 600/532 |
| 5,152,963 A | | 10/1992 | Wreyford .................... 422/80 |
| 5,227,135 A | | 7/1993 | Godec et al. ................. 422/98 |
| 5,310,683 A | | 5/1994 | Godec et al. ............... 436/123 |
| 5,330,714 A | | 7/1994 | Godec et al. ................. 422/52 |
| 5,395,501 A | | 3/1995 | Rohrbacker et al. ........ 204/265 |
| 5,397,708 A | | 3/1995 | Lessard et al. ............... 436/30 |
| 5,409,591 A | | 4/1995 | Baker et al. ................ 204/425 |
| 5,424,217 A | | 6/1995 | Benner et al. .............. 436/123 |
| 5,466,350 A | | 11/1995 | Baker et al. ........... 204/153.14 |
| 5,501,981 A | | 3/1996 | Ray et al. ................... 436/123 |
| 5,580,433 A | | 12/1996 | Baker et al. ................ 204/425 |
| 5,614,417 A | | 3/1997 | Kubala et al. .............. 436/120 |
| 5,632,875 A | | 5/1997 | Chapples et al. ........... 204/431 |
| 5,661,036 A | | 8/1997 | Benner et al. .............. 436/123 |
| 5,668,302 A | | 9/1997 | Finbow et al. ............... 73/23.2 |
| 5,916,523 A | | 6/1999 | Yan et al. ..................... 422/83 |
| 5,935,519 A | | 8/1999 | Benner et al. ................ 422/52 |
| 6,013,530 A | | 1/2000 | Tawara ....................... 436/123 |
| 6,057,162 A | | 5/2000 | Rounbehler et al. ........ 436/119 |
| 6,130,095 A | | 10/2000 | Shearer ...................... 436/123 |
| 6,143,245 A | | 11/2000 | Yan et al. ..................... 422/52 |

OTHER PUBLICATIONS

"Standard test method for total trace nitrogen and its derivatives in liquid aromatic hydrocarbons by oxidative combustion and electrochemical detection," American Society for Testing and Materials, Designation: D 6366–99, 1999.

"Test method for total sulfur in liquid aromatic hydrocarbons and their derivatives by oxidative combustion and electrochemical detection," American Society for Testing and Materials, Designation: D 6428–99, 1999.

"Standard test method for trace nitrogen in liquid petroleum hydrocarbons by syringe/inlet oxidative combustion and chemiluminesence detection," The American Society for Testing and Materials, Designation: D 4629–96.

"Standard test method for determination of total sulfur in light hydrocarbons, motor fuels and oils by ultraviolet fluorescence," The American Society for Testing and Materials, Designation: D 5453–93.

Fontijn, et al., "Homogenous chemiluminescent measurement of nitric oxide with ozone," *Analytical Chemistry*, vol. 42, No. 6, 575–79, May 1970.

Schwarz, et al., "Fluorescence detection of dulfur fioxide in air at the parts per billion level," *Analytical Chemistry*, vol. 46, No. 8, 1024–28 Jul. 1974.

\* cited by examiner

METHOD AND APPARATUS FOR THE ON-STREAM ANALYSIS OF TOTAL SULFUR AND/OR NITROGEN IN PETROLEUM PRODUCTS

BACKGROUND OF THE INVENTION

Sulfur in motor fuels such as gasoline and diesel fuel is an important pollutant. Its concentration has been regulated over the past several years so as not to exceed levels in the range of 500 parts per million (ppm). In order to ensure that the regulated concentration levels are not exceeded, petroleum products are subjected to both laboratory and on-stream analysis during their processing and production. At these concentrations, one of the preferred methods of analysis is x-ray fluorescence spectrometry, described in ASTM methods D 2622 and 4294 incorporated herein by reference, which is well-suited to direct analysis of liquid samples. However, recent government regulations worldwide will reduce the acceptable sulfur contents of gasoline and diesel fuel to below 50 ppm with specific regulatory levels set at 30 and 15 ppm in the next two or three years. It is doubtful whether x-ray fluorescence is sensitive enough to reliably monitor sulfur at 15 ppm, see ASTM Research Report D.02-1456, incorporated herein by reference. There is also a need to monitor total nitrogen, in the ppm range, in liquids such as beverages and fuels. X-Ray fluorescence is not suitable for measuring nitrogen content.

Other more sensitive laboratory methods are "pyro-UV fluorescence" for sulfur, according to ASTM method D 5453 incorporated herein by reference, "pyro-chemiluminescence" for nitrogen, according to ASTM method D4629 incorporated herein by reference, and "pyro-electrochemical" for either or both sulfur and nitrogen, described in ASTM methods D6366 and 6428 also incorporated by reference herein. In all these methods a small fixed volume of sample is thermally oxidized ("pyrolyzed") and the combustion products are analyzed for $SO_2$ or NO. Ultraviolet fluorescence for $SO_2$ and chemiluminescence for NO both have detection limits of 1 ppb or less, so the sensitivity is good enough to monitor low ppm levels of sulfur or nitrogen in liquids even allowing for the dilution inherent in the pyrolysis step. Similarly, the sensitivity of electrochemical detectors, although not as good as UV fluorescence or chemiluminescence, should be adequate to measure low ppm levels of sulfur and/or nitrogen in liquids, after pyrolysis. However, electrochemical detectors have the great advantages of simplicity and low cost.

Known systems for employing these methods, however, have many drawbacks that are avoided by the present disclosure. In particular, known systems fail to guarantee the quality of the pyrolysis, and as a consequence, reproducible and reliable results may not be obtained and sooting may occur. In employing these analysis methods, a dryer is utilized after pyrolysis to insure the quality of the analysis is not adversely affected by the presence of too much water vapor. However, the dryer arrangement employed in known systems is either costly requiring the use of a separate vacuum pump or may fail to prevent the collapse of the sample dryer inner tube.

SUMMARY OF THE INVENTION

The present invention overcomes the drawbacks of known analysis methods by providing reliable and cost-effective on-stream analysis methods and apparatuses for measuring chemical components, including the measurement of total sulfur and nitrogen contents and other components that may be monitored. The present invention accomplishes these objectives by, in certain embodiments, providing reproducible and reliable pyrolysis products and/or by providing an improved dryer design. On-stream analyzers preferably operate automatically and reliably and therefore may include many features, components and improvements that enable the erstwhile laboratory method to function successfully as an on-stream analyzer. Such improvements and additional features are described below.

On-stream analysis for monitoring pollutant levels is of particular importance in many industrial applications. For example the monitoring of sulfur and nitrogen is of concern within the petroleum and beverages industry, however other applications are contemplated by the present disclosure. For simplicity, we refer primarily to monitoring sulfur, although it is contemplated and within the scope of the present invention that the disclosed methods and apparatuses may also be employed for the analysis of other chemical components which may be measured by measuring their pyrolysis products and are capable of detection according to the techniques disclosed herein.

According to the ASTM method, a fixed volume, usually 5–20 microliters, of liquid sample is injected into the pyrolyzer along with an inert carrier gas, usually argon at a flow rate of about 130–160 sccm (standard cubic centimeters per minute) and including some oxygen, about 10–30 sccm. The liquid vaporizes and then reaches the combustion zone where another flow of oxygen, about 450–500 sccm, the "pyrolysis-gas", is introduced and effects complete thermal oxidation at 1050° C. The reactor is a quartz tube heated by a tube furnace. The flow rate of liquid sample should never exceed about 4 $\mu$l/s (microliters/second), otherwise the combustion process will be starved of oxygen and soot formation (or "sooting") will occur, that is, the internal surfaces downstream of the hot zone will be covered with soot. The ASTM methods specify a flow rate of 1 $\mu$l/s. The gas output from the pyrolyzer is a mixture of the inert carrier gas (about 20 vol %), unconsumed oxygen (about 60 vol %), carbon dioxide, $CO_2$ (about 10 vol %), water vapor (about 10 vol %) and ppm levels of $SO_2$. The dewpoint is 45–50° C., so the gas lines are usually heat traced and/or the water vapor content is reduced to prevent condensation. Water vapor can be reduced without affecting the $SO_2$ content by means of a permeation dryer which operates on the principle of absorption-desorption of water vapor through a membrane (a rapid process having first order chemical kinetics), such as the "NAFION" membrane dryer, commercially available from Perma Pure, Inc. The conditioned gas mixture is then fed to the $SO_2$ detector. A typical 20 $\mu$l sample takes some 20 seconds to inject and passes through the pyrolyzer and other gas sample plumbing in about one minute. The $SO_2$ concentration at the detector starts at zero just before the injection, rises to a maximum and then falls off to zero. The rates of rise and fall depend on the various flow rates and gas mixing, and on any molecular exchange reactions that the $SO_2$ undergoes at surfaces it comes into contact with. The detector response ideally follows this same profile. The actual detector response will be less than ideal, so additional broadening of the time profile will occur. In practice, the whole $SO_2$ signal from a given injection will extend over 2–5 minutes. This signal is integrated and is directly proportional to the total amount of sulfur in the original sample. As long as the sample volume remains constant, the $SO_2$ signal is, therefore, proportional to sulfur content of the original sample. "Continuous" analysis is accomplished by automating the sample injection procedure.

It is therefore an object of the present disclosure to provide reproducible and reliable pyrolysis byproducts for use in an on-stream analyzer by, in certain embodiments, controlling the volume of a liquid sample dispensed for injection into a pyrolyzer so that it is constant and repeatable. Also, the injection rate is preferably controlled below the upper limit set by "sooting" and above a lower limit below which the analysis takes too long. In practice, there are closer tolerances set not only on the sample injection rate but also on the flow rates of the input gases. If the detector background signal is negligible, the size of the integrated signal, e.g. $SO_2$ or other chemical signal, would depend only on the total sample volume injected (and its sulfur or other chemical content). Variations in injection rate and in flow rates of the input gases will cause changes in dilution of the $SO_2$ or other components to be measured in the output gas but this would not matter as long as the total signal were to be integrated. In practice, the background signal is not negligible and the amount of time available to complete the integration is limited, so all of it may not be captured. It follows that the dilution of the $SO_2$ or other component in the sample is a factor that may preferably be controlled.

Laboratory instruments employ a microliter syringe, usually motorized, to pump a reproducible volume at a reproducible flow rate. This is not practicable in a process analyzer. Instead, the fixed volume sample can be realized by the use of a sample loop and a two-position (two cycle) multiport valve. The loop is filled from the process stream during one valve cycle and emptied into the pyrolyzer during the second cycle. This is described in U.S. Pat. No. 5,152,963 to Wreyford, incorporated herein by reference. However, specific control of the sample injection rate is apparently not described in U.S. Pat. No. 5,152,963.

A further object of the present disclosure is to offer an improved means for sample injection rate control. In one embodiment the sample injection rate is controlled as follows: Inert gas, such as argon or helium which is readily available, is introduced at a constant pressure, via a pressure regulator, to a flow restrictor such as a length of capillary tubing or a micro-metering valve (an especially preferred embodiment includes use of a micro-metering valve manufactured by Upchurch Scientific that is capable of being turned down to flow rates of less than 1 $\mu l/s$). The gas, thus flowing at a constant rate, pushes the liquid sample out of the fixed volume sample loop, through the injector tube and into the pyrolyzer. Since the volume of sample is fixed, the back pressure produced by it is constant until it begins to flow out of the injector. Then the back pressure goes steadily to near zero. The maximum back pressure is below about 0.4 psi for fuel samples with normal viscosity, about 2 cP (centipoise). The regulated pressure should be in the range 5 to 15 psig, preferably about 8 psi so the relative change in back pressure is less than 10% and is repeatable from sample to sample. The flow rate is calibrated prior to operation using a bubble-meter and stopwatch or by timing the appearance and development of the liquid sample drop at the injector tip with the injector out of the pyrolyzer. This assembly provides an injection rate constant to about 10–20%.

Other methods of controlled injection operate by positive displacement of the liquid sample using a piston. Apart from the abovementioned microliter syringe, operated automatically by a syringe pump or manually, one could employ a piston pump or dispenser such as the FMI Model PiP00SKY. Each of these alternate methods are contemplated by the present invention.

U.S. Pat. No. 5,152,963 and the ASTM methods employ standard laboratory rotometers (floating ball flow meters) with metering valves for flow control of the carrier gas and oxygen. At the flow rates stated above, a 10% change in each of the input gases will produce the following changes in output sample flow rate and resulting equal changes in $SO_2$ or NO content through dilution: argon carrier gas, 2%; oxygen pyrolysis gas, 7% and oxygen carrier gas, 0.4%. Errors of this magnitude will show up in the measured sulfur or nitrogen content. An additional object of the present disclosure is to measure each gas flow with an electronic flow meter. The flow data are fed to the Programmable Logic Controller, PLC, and are available to make corrections as necessary to the $SO_2$ reading. Also contemplated is the use of flow alarms to indicate failure of any gas flow and to greatly reduce the danger of catastrophic equipment failure due, for example, to "sooting". Furthermore, the output gas flow may also be monitored. This enables flow balance calculations to be made with the resulting ability to detect gas leaks, for example. Finally, the quality of the pyrolysis can be checked by monitoring small fluctuations in the output gas flow that occur during pyrolysis.

Other alternate or preferred embodiments of the present disclosure include one or more of the following. (1) The pyrolysis furnace may be enclosed in a sealed container whose outside surface temperature never exceeds 200° C. (this is the "surface temperature classification", T3, defined for hazardous locations relevant to our application). Thus, if the enclosure purge fails and the electrical power is consequently cut off, the furnace will still be at over 1000° C. and will take hours to cool down. In a hazardous location, such as an oil refinery, explosive vapors could reach the furnace and cause an explosion even when the electrical power is off. Sealing the furnace is an acceptable method for maintaining equipment safety. (2) A combustible gas sensor may be installed in the enclosure to indicate and provide an alarm for any leak of possibly explosive vapors into this enclosure. (3) The heat trace element for the gas sample stream may comprise a self-limiting cable for extra safety. Such a cable, for example, Omega, Cat# SRL5-2, comprises two parallel conductors separated by a partially conducting polymer. As the temperature increases the resistance between the conductors increases, reducing the heating current. The upper temperature may be limited to about 66° C. (4) The gas sample stream dryer may be operated in a novel manner to avoid problems due to back pressure caused by dryer tube collapse (see detailed description, later). (5) The $SO_2$ or NO detector may be an electrochemical cell, not a UV fluorescence analyzer. (6) A humidifier may be included just upstream of the electrochemical cell to prevent the relative humidity of the gas filling too low between liquid sample injections, when only dry argon and oxygen are flowing, or when calibration gas is being introduced from a compressed gas cylinder. (7) The relative humidity of the gas sample stream may be monitored and alarm signals available if the relative humidity exceeds a preset upper or lower limit. (8) Liquid sample and calibration sample routing outside the instrument enclosures may be performed by pneumatically operated valves, controlled from within the enclosures, which are intrinsically safe. (9) The calibration liquid samples may be pumped using air pressure, also intrinsically safe. (10) The flow rate of calibration liquid may be preset and controlled separately from that of the process fluid in order to conserve expensive calibration liquid and lengthen the time interval required between refilling the calibration reservoirs. (11) The injector may be mounted so that its tip penetrates the pyrolyzer just far enough to where the pyrolyzer temperature is high enough to smoothly volatilize the liquid sample but not so high as to cause chemical breakdown inside the injector.

One preferred embodiment of the disclosed on-stream analyzer which measures the concentration of a substance in a fluid sample includes a sample injector, a thermal oxidizer, a sample conditioner, a detector, and a programmable logic controller. The sample injector injects the sample at a preset and controlled rate, the sample injector optionally includes a pressure regulator coupled to a flow restrictor, effective to restrict the flow rate of the sample, thereby slowing, reducing, or eliminating the sample flow. Examples of preferable flow restrictors include a metering valve or a length of capillary tubing having a diameter of about 0.001 to about 0.020, preferably 0.004 inches, to control the rate of sample flow. The thermal oxidizer may be enclosed within a container, designed to have an outer surface temperature that does not exceed the lower explosive temperature of the sample being analyzed and to prevent ingress of vapors of the sample being analyzed, and has a tube furnace and a pyrolysis tube, connected to the sample injector so that the sample is injected into the pyrolysis tube, volatilized, and a carrier gas, i.e. an inert gas which is preferably argon, helium, or mixtures thereof and optionally containing an admixture of oxygen, and a pyrolysis gas, preferably oxygen, are introduced at a preset, controlled rate, under oxidation conditions. Metering valves are utilized to control the flow rates of the carrier and pyrolysis gases and electronic flowmeters, connected to the programmable logic controller, are employed to measure the flow rates of the carrier and pyrolysis gases as well as the total flow rate of the gas mixture. The electronic flow meters may optionally include an alarm that indicates a flow rate of either carrier or pyrolysis gases that falls outside a preselected range. Oxidation conditions may include a temperature ranging from about 1000° C. to about 1200° C. and preferably about 1050° C. The sample conditioner, connected to and located downstream from the thermal oxidizer, controls the conditions of the resulting gas mixture. The sample conditioner preferably includes one or more of the following, a filter, a dryer, and/or a heat trace element. The filter is preferably made of a chemically inert material, such as polytetrafluorethylene, and prevents solid particles or liquid drops from passing downstream thereby preventing contamination of downstream components and/or surfaces. The heat trace element is preferably composed of self-limiting electrical heating wires that are effective to maintain the gas stream above its dewpoint from the pyrolysis tube to the dryer. The dryer preferably contains two concentric tubes, an inner tube and an outer tube. The inner tube composed of a membrane for transferring water vapor, preferably the membrane contains active groups for effectuating the water transfer and the active groups are preferably sulfonic acid groups. The outer tube is composed of an inert material that is preferably a fluoropolymer or 316 stainless steel. It is preferable for the dryer to be configured so that a dry purge gas passes through the inner tube and the sample gas is directed through the annular space between the outer tube and the inner tube. Further, the dryer may optionally contain a restrictor, connected to the inner tube to maintain positive pressure within the dryer. The restrictor preferably includes an orifice having a diameter of about 0.001 inches to about 0.05 inches, preferably 0.0122 inches. The dryer may optionally include metering valves to control the purge gas flow and electronic flowmeters, connected to the programmable logic controller, to measure the purge gas flow. The electronic flow meters preferably include an alarm to indicate a purge gas flow that falls outside a preselected range. The detector is connected to the sample conditioner and measures the concentration of oxidized substance contained within the resulting gas mixture. The detector preferably includes an assembly of one or more electrochemical cells where the electrochemical cells are preferably sensitive to $SO_2$ or NO and may contain an arrangement of electrochemical cells capable of detecting both $SO_2$ and NO. The programmable logic controller, connected to the detector, calculates the concentration of oxidized substance contained within the gas mixture and consequently the concentration of substance in the original fluid sample.

Another preferable feature that may be optionally included is a combustible gas sensor to indicate the presence of combustible gas vapors. In addition, it is preferable to utilize a humidifier, located upstream from the detector, to maintain the relative humidity level between about 15 to about 90%. The humidifier may optionally include a relative humidity sensor with an alarm to indicate a relative humidity level that falls outside a preselected range.

It is also preferable to utilize non-electric valves to route the fluid sample to the thermal oxidizer, the non-electric valves are preferably pneumatically operated and therefore intrinsically safe. The analyzer also preferably includes a fluid sample outlet and a non-electric flow indicator to indicate the flow rate of the sample through the fluid sample outlet.

Another optional feature is one or more pneumatic valves for introducing one or more calibration fluids, contained in one or more calibration sample reservoirs (storage vessels), to the injector by means of non-electrical valves, more preferably pneumatically operated valves. The flow rate of the calibration fluids may optionally be controlled with metering valves. Also, a preferred embodiment may include solenoid valves, controlled by the programmable logic controller, to effectuate flow of the calibration gas directly to the detector, bypassing the thermal oxidizer and sample conditioner. Further, pneumatically-actuated pressure switches to send signals, via the solenoid valves, to the programmable logic controller to indicate low gas pressure is also preferred.

Another embodiment of the present disclosure involves a method for drying a gas mixture including the steps of providing a gas mixture to be dried, passing a purge gas through an inner tube, feeding the gas mixture through the annular space between the inner tube and an outer tube, restricting the purge gas flow, and capturing the dried gas mixture. The inner tube is comprised of a membrane for transferring water and preferably the membrane contains sulfonic acid groups. The outer tube is comprised of an inert material, preferably a fluoropolymer or 316 stainless steel. It is preferable that the restricting of the purge gas flow is accomplished with a restrictor having an orifice, between about 0.001 to about 0.05 inches in diameter, more preferably 0.0122 inches, to maintain positive pressure.

DETAILED DESCRIPTION OF THE PREFERRED EMBODIMENT

Referring to accompanying FIGS. 1-4, the operation of the sample injector, or "Fast Loop" is first described. For the embodiments analyzing petroleum products, the sample material is likely to be gasoline or diesel fuel and therefore highly flammable. In those embodiments, no electricity is preferably involved in the valving or pumping outside the instrument enclosures, 10 and 20. For safety, the rotary valves, 40 and 45, and the air valves, 50, are pneumatically operated, and calibration samples are pumped by air or inert gas pressure from the storage vessel, 60. The compressed air or inert gas for this is controlled from within the instrument enclosure by solenoid valves, 70. The process stream sample for analysis is provided under a few psig pressure to rotary valve 40 via valves 45 (optionally), and 50. If several process streams are to be serviced each one may be connected to the multiposition rotary valve, 45, whose position is pneumatically controlled from the main computer (or "PLC"), 80, (note, electrical connections are not shown) via the control modules 90 and 100. The selected process stream flows through filter, 110, to the 6-port, 2-position valve, 40. The pneumatic valves, 50, operated by compressed air or compressed inert gas, are set by solenoid valves, 70, to allow this. The main computer, or Programmable Logic Controller, 80, is programmed to sequence all the solenoid valves in the instrument and control all the functions to be described herein. In the "flush" position of rotary valve, 40, port 1 is connected to port 6 and port 2 to port 3, so that the sample flows through the fixed volume loop, 120, and back to the process via the pneumatic valves, 50, to guard against backflow from the process, and the mechanical flow indicator, 130. The flow indicator is typically a transparent tube, usually glass, with a floating ball, therefore intrinsically safe. Its importance is to show the approximate flow rate of both process fluid and calibration samples and also to indicate the absence of undesirable bubbles in the liquid stream. The 1 $\mu$l/s, in this example, controlled gas flow from the low pressure regulator, 140, and the micro-metering valve, 150, flows into port 1 of rotary valve, 40, and out of port 5 into the pyrolysis tube, 160. When rotary valve, 40, changes to its "inject" state, ports 1 and 2 are connected together, causing further sample to bypass the valve, while port 4 is connected to port 3 and port 5 to port 6. The gas from micro-metering valve, 150, then delivers the fixed sample volume, in this example 20 $\mu$l, out of the loop, 120, and through the injector tube, 540, into the pyrolysis tube, 160, via the fitting, 170, at a preset flow rate of, in this example, 1 $\mu$l/s. Thus a sample of fixed volume is injected at a controlled rate. Typical timing for the two states is preferably about 90 seconds for the injection and about 210 seconds for the flush, giving a total sample measurement cycle time of about 5 minutes, however any suitable timing can be employed.

Figure 1:
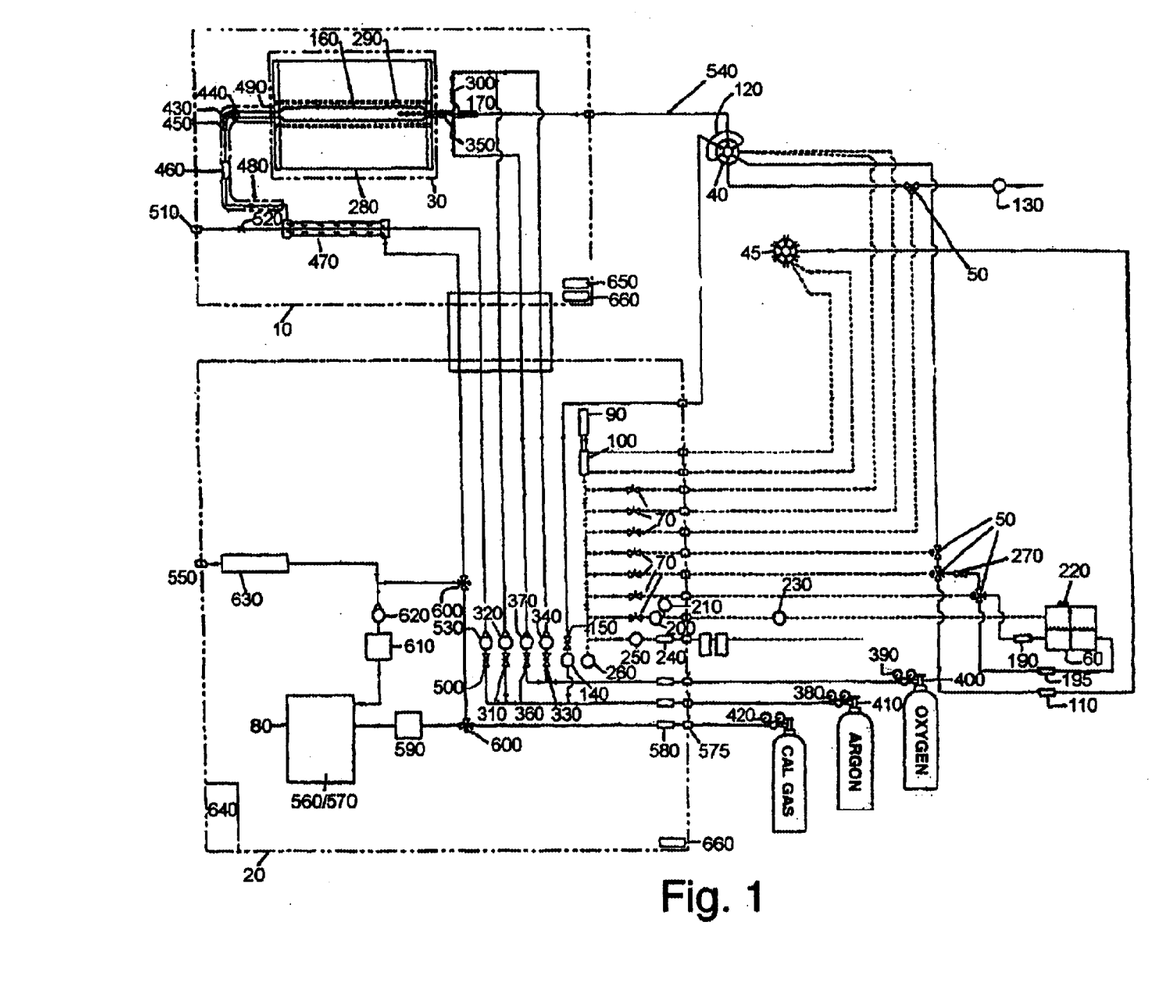
FIG. 1 is a diagrammatic view of an apparatus according to the disclosure.
Figure 2A:
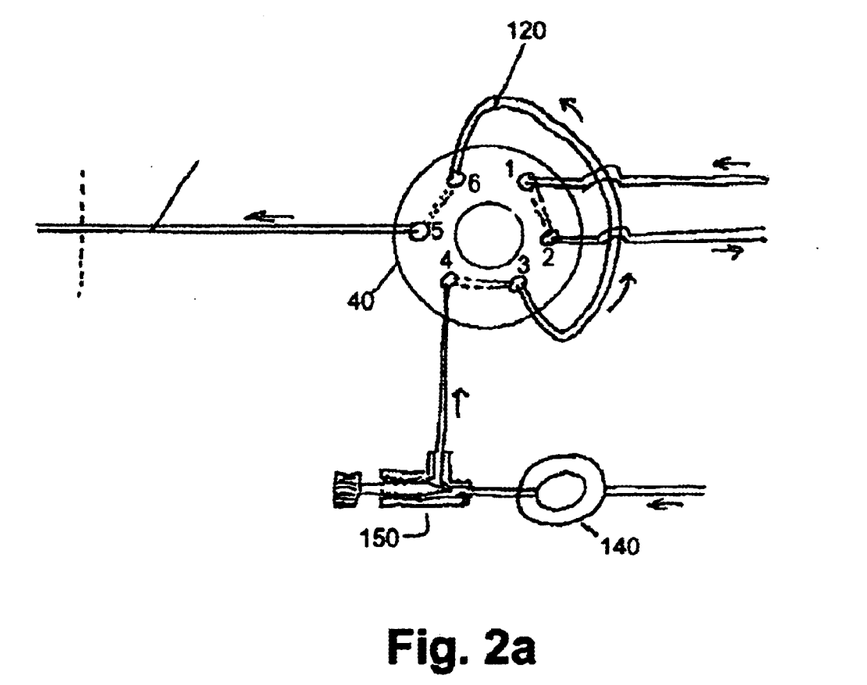
FIG. 2(a) is a section, to a larger scale, of the sample injection loop configured for an injection cycle.
Figure 2B:
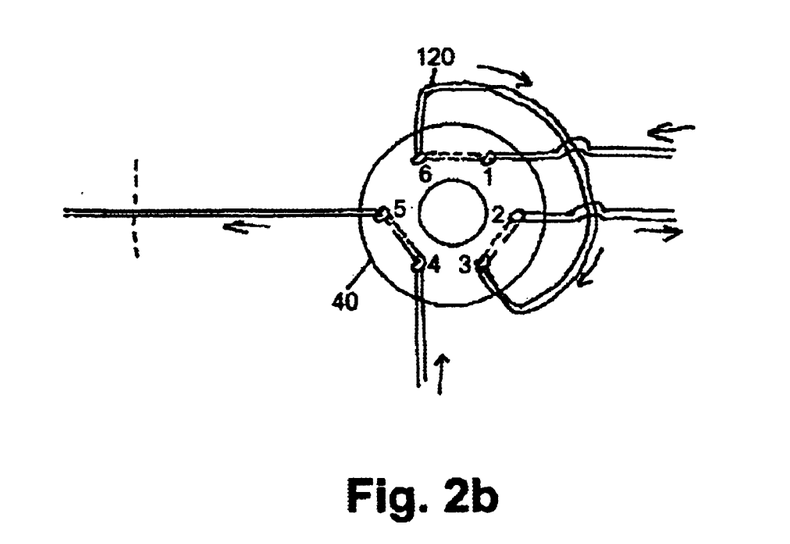
FIG. 2(b) is a section, to a larger scale, of the sample injection loop configured for a flush (loop recharge) cycle.

Calibration samples having known sulfur and/or nitrogen concentrations are stored in the storage vessel, 60. In one embodiment, two concentration levels are stored, although the storage vessel can have any number of compartments, with appropriate valving, to store any number of calibration samples. In normal operation two concentrations may be stored, a high and a low (or zero), to match the upper and lower limits of sulfur or nitrogen content expected in the materials being analyzed. In a calibration cycle, pneumatic valves, 50, are switched by solenoid valves, 70, under PLC control, so as to supply either the "high car" or the "low car" sample to rotary valve, 40. Filters 190 and 195 are similar to filter, 110. Calibration sample flow is produced by about 5 to 15 psig of air pressure supplied to the head space in storage vessel, 60, by solenoid valve, 70, and pressure regulator, 200. Pressure switch, 210, sends an alarm signal to the PLC, 80, if the set pressure is too low. Pressure relief valve, 220, prevents any excess pressure build-up in storage vessel, 60. Check valve, 230, prevents any potentially explosive vapors from storage vessel, 60, getting back into the instrument enclosure. Instrument air or inert gas is supplied to power the optional control module, 100, and solenoid valves, 70, via the optional air cleanup cartridges, the filter, 240, and the pressure regulator, 250. The pressure switch, 260, sends an alarm signal to the PLC, 80, if the input instrument air or inert gas pressure is too low. The flow rate of calibration liquid is preset and controlled by metering valve, 270. The calibration samples are close to the injection valve whereas the process stream normally may travel a relatively long distance, possibly tens of feet, to the analyzer. Therefore the flow rate of process stream must generally be much higher than that of the calibration samples in order that the analyzed sample is current. The provision of metering valve, 270, ensures that the calibration sample flow rate can be lower than that of the process stream, so reducing consumption of expensive calibration liquids. Typical flow rates are 40 ccs/min for the process stream and 4 ccs/min for the calibration streams.

Pyrolysis or thermal oxidation of the sample is accomplished as follows. Tube furnace, 280, is operated at 1000 to 1100 degrees C., per the ASTM method. The thermocouple, 290, measures the temperature and sends the signal to the PLC, 80, which controls the temperature. Electrical heater and control wires are not shown. The pyrolysis tube, 160, is a 1 inch diameter by 12 inch long quartz tube (as described in the ASTM method) and may optionally be filled with small quartz tubules (approximately 0.5 inch long by 0.25 inch diameter) designed to increase the surface area available for the thermal oxidation reactions. Inlet gas, a mixture of argon and oxygen, is introduced through the fitting, 300, from the metering valve, 310, and flow meter, 320, and the valve, 330, and flow meter, 340. Per the ASTM method the argon flow rate is about 150 sccm and the oxygen flow rate about 20 scc The valves are manually preset to these rates and the flow meters send their signals to the PLC, 80, which stores and monitors them, alarming if they go out of preset limits. The flow rate signals can also be employed to make corrections to the analysis results. This inlet gas mixture carries the sample, which by the time it reaches the end of the injection tube has vaporized, into the oxidation part of the pyrolysis tube. Pyrolysis gas, a flow of 450 to 500 sccm of oxygen, is introduced at the fitting, 350, and accomplishes complete oxidation of the sample to the products carbon dioxide, water vapor and sulfur dioxide (and nitric oxide if nitrogen is present). The oxygen flow is controlled by the preset metering valve, 360, and monitored by flowmeter, 370. Argon and oxygen are provided by compressed gas cylinders through two-stage pressure regulators, 380 and 390, respectively. It is well known that the delivery pressures to metering valves must be regulated so that the metering valves can ensure a stable gas flow. The optional pneumatic (therefore intrinsically safe) pressure switches, 400, 410 and 420, send alarm signals to the PLC, 80, if the gas supply pressures fall below acceptable limits. This would usually happen when the compressed gas cylinders are nearly empty and require replacement.

Recognizing that there is a temperature gradient along the axis of the tube furnace from somewhat above ambient temperature at each furnace end wall to the maximum temperature region (1000 to 1200° C., depending on the temperature control setting) in the middle of the furnace, the injector tip must be placed at a distance in the pyrolysis tube from the furnace wall such that its temperature is high enough to cause smooth sample volatilization as it is injected but not so high that the sample is broken down chemically in the inert atmosphere inside the injector tube, causing carbon formation (if the sample is a carbon compound) and consequent injector blockage. A preferable temperature range for the injector tip is from about 400 to about 450° C. for diesel fuel samples but the tip can be placed at a point where the temperature is in the range from just above the sample boiling point (diesel boils at temperatures up to about 330° C.) to just below the sample breakdown temperature (about 500–600° C. for hydrocarbons).

Figure 3:
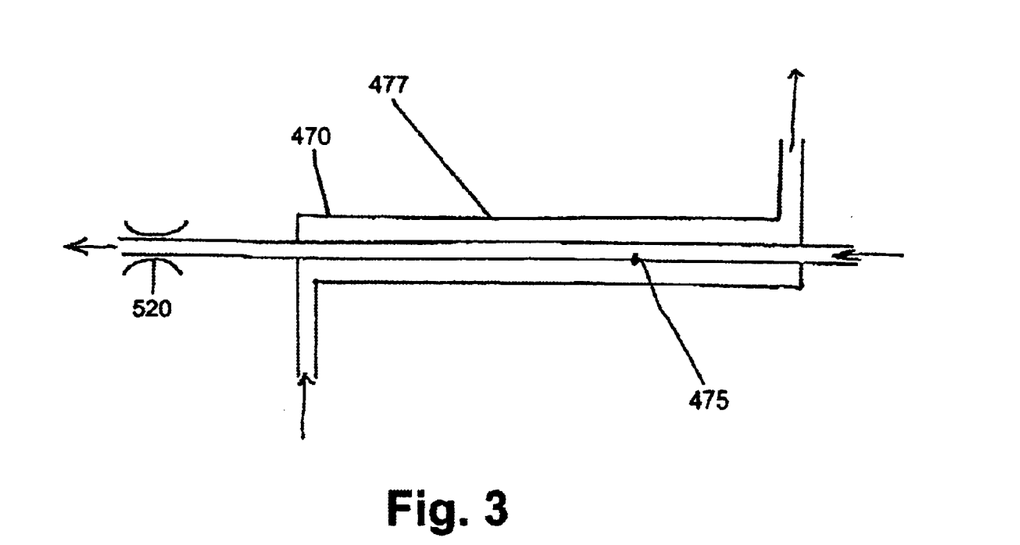
FIG. 3 is a section, to a larger scale, of the dryer configuration.

The product of the thermal oxidation is a gas mixture of approximate composition: 60% oxygen, 20% argon, 10% carbon dioxide and 10% water vapor, plus ppm quantities of sulfur dioxide and, if nitrogen is present in the original process stream, nitric oxide. This flows at a rate of (in this example) 550–650 sccm out of the pyrolysis tube, 160, through the Pyrex socket (elbow), 430 (which is clamped to the tube with a pinch clamp, 440), through the outlet fitting, 450, into the membrane filter, 460. Here any particulates are filtered before the gas flows through the membrane dryer, 470, where the water vapor content is reduced to below the ambient dewpoint. The sample path including tubing and filter holder between the outlet of the pyrolysis tube and the inlet to the Dryer is heat traced, 480, and insulated to maintain a temperature of at least about 50° C. (but not exceeding about 66° C.) so as to prevent water condensation. The heat trace element, 480, is self-regulating heat trace cable whose temperature should not exceed about 66° C. Thermocouple, 490, is connected to the PLC, 80, that monitors the heat trace temperature and alarms if it goes out of preset limits. The dryer, 470, exchanges water vapor, but none of the other gases present, through its membrane with the dry purge gas that is flowing at a rate of 250–500 sccm on the other side of the membrane. The purge gas in our example is argon, although dry air or other suitable dry gas may be used. The purge gas may be supplied from the argon compressed gas cylinder through the metering valve, 500. The purge gas vents to atmosphere through vent, 510, after passing through the flow restrictor, 520. Flow meter, 530, monitors the flow rate and sends its signal to the PLC, 80, which provides an alarm signal if the flow rate goes outside preset limits.

Figure 3A:
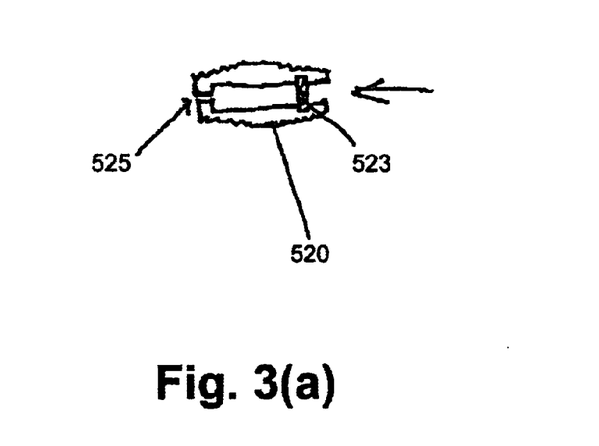
FIG. 3(a) is a section, to a larger scale, of the restrictor configuration.

Drying of the sample gas stream without causing back pressure problems and without resorting to vacuum pumps is accomplished in a novel manner as follows. The dryer, 470, has two concentric tubes, for example, Permapure Model MD-110-24F-4. The inner tube, 475, is composed of a membrane for transferring water vapor that operates on the principle of absorption-desorption and the outer tube, 477, is made of a material that is inert to the sample gases, especially $SO_2$, such as 316 stainless steel or a fluoropolymer. One optional embodiment employs perfluoroalkoxy, PFA, for the outer tube. An embodiment for the inner tube may utilize a nonporous membrane that removes gases based upon their chemical affinity for active groups, such as sulfonic acid groups, interspersed within the membrane matrix. One especially preferred embodiment includes a perfluorinated membrane with sulfonic acid groups such as a NAFION membrane. The inner tube is about 0.110 in OD×0.100 in ID and normally carries the sample to be dried. The outer tube is about 0.250 in OD×0.190 in ID. The annular space between the outer and inner tubes normally carries the drying (purge) gas. The inner tube can withstand an internal pressure of at least 100 psig but will collapse if the external pressure on it is greater than the internal pressure by more than about 0.2 psi. This is not a problem in the normal operation mode of these dryers, which is to pull the purge gas through by means of a vacuum pump, in which case the inner tube is always at a greater pressure than the annulus. However, the gases of the claimed invention are introduced at a positive pressure and "pushed" through the system by this pressure. In addition, it is important to have as low a back-pressure as possible at the sample injector tube, 540, to ensure a stable, repeatable injection rate. Therefore all components in the sample gas stream downstream of the injector must be designed for lowest possible pressure drop. The dryer design of the claimed invention prevents collapse of the inner tube while at the same time minimizing sample gas pressure drop by directing the sample gas through the outer annulus while the purge gas is sent through the inner tube at a guaranteed positive pressure. That is, the dryer is operated "inside out". The positive pressure in the inner tube is guaranteed by the restrictor, 520, which is an orifice, 525, with a hole small enough to produce a pressure drop of 1–3 psi at the purge gas flow rates used. Such an orifice is available from O'Keefe Controls, Model BS-12-BR, with a hole diameter of 0.0122 in. Orifices with this and other hole diameters of from about 0.001 to about 0.050 inches, depending on the purge gas flow rate, are acceptable for use and available at relatively low cost. The flow restrictor may optionally include a screen, 523, to prevent particles from clogging the orifice. The overall pressure drop of the sample gas from the inlets of the pyrolysis tube, 350, 300 and 170, to the exhaust to atmosphere at 550 is preferably kept at or below about 0.5 psi. The pressure drop across the inner tube membrane should be kept as small as possible so as not to hinder the transport of water vapor molecules across the membrane from the annulus to the inner, dry purge gas. Note that it does not matter in which direction the water vapor molecules travel across the membrane since their transport depends only on the gradient of the water vapor partial pressure. Note also that, since the cross sectional area of the annulus (0.122 $cm^2$ in our example) is greater than that of the inner tube (0.051 $cm^2$), the pressure drop of the sample gas through the dryer is further reduced from that which it would be if the dryer were operated in its normal mode. Counter flow between the purge and sample gases is preferred but not essential. In this way the driest purge gas first meets the sample gas just before it exits the dryer, ensuring maximum drying efficiency.

The entire sample path between the pyrolysis tube and the $SO_2$ or NO detector, 560 or 570, preferably comprises a fluorinated polymer or 316 stainless steel wetted parts, to prevent loss or "hang-up" of $SO_2$ or NO caused by molecular exchange reactions between the $SO_2$ or NO and any surface it comes into contact with. Condensed water vapor film and any soot particles should be prevented from forming for the same reason.

The $SO_2$ detector, 560, and optionally NO detector 570, if present, is any suitable electrochemical sensor such as the City Technology Model A3ST/F (for $SO_2$) or Model 3NF/F (for NO). The sample gas passing through the sensor preferably has a relative humidity between 15 and 90%. As described above, when thermal oxidation is occurring, the relative humidity is above the dewpoint at ambient temperature so the gas should be dried, which is the purpose of the dryer, 470. However, when the pyrolysis gases argon and oxygen are flowing without a liquid being injected for thermal oxidation, the gases reaching the sensors could be very dry, well below 15% relative humidity. Also, if calibration gas from a compressed gas cylinder is introduced directly to the sensor via 575, 580 and 600, it will have an relative humidity below 15%. Therefore, a humidifier, 590, is included in the sample inlet line to the sensor. This employs a membrane similar to the dryer, except that water is present on the opposite side of the membrane to the sample gas. Water vapor molecules are transported through the membrane to humidify the gas without loss of any $SO_2$ or NO. By these means the gases reaching the sensors always have a relative humidity between 15 and 90%. The solenoid valves, 600, are switched to send sample or calibration gas through the sensor module, and to bypass sample gas when calibration gas is going through the sensor module. Note that the analysis may be performed by an assembly having more than one sensor of each type, that is an $SO_2$-type or NO-type may be incorporated in the sensor assembly. For example, sensors having different sensitivities can be used for monitoring high and low concentration ranges; two or more sensors can be challenged with sample gas in sequence, so as to allow more time for any one sensor to recover to its baseline reading between samples; spare sensors can be mounted and switched into use in the event of sensor failure.

The sample gas leaving the sensor enclosure passes though a relative humidity sensor, 610, and a flow meter, 620, before being scrubbed free of noxious $SO_2$ and/or NO in the scrubber cartridge, 630, which contains granules of any scrubber material, suitable for removing $SO_2$, NO and excess $CO_2$. The cleaned gas is then exhausted to atmosphere through exhaust, 550. The flow rate signal from flowmeter, 620, goes to the PLC, 80, and thereby monitors total sample flow. This is useful for detecting any leaks in the system, since the total of the input flows is also known. Also, the quality of the pyrolysis "burn" can be monitored since, when the liquid burns it produces an increase in flow rate that matches the temporal burn profile, including fluctuations if the burn is uneven. In addition, absence of pyrolysis when it should be present (an indication of a blocked injector tube or lack of sample, for example) is readily detected.

Figure 4:
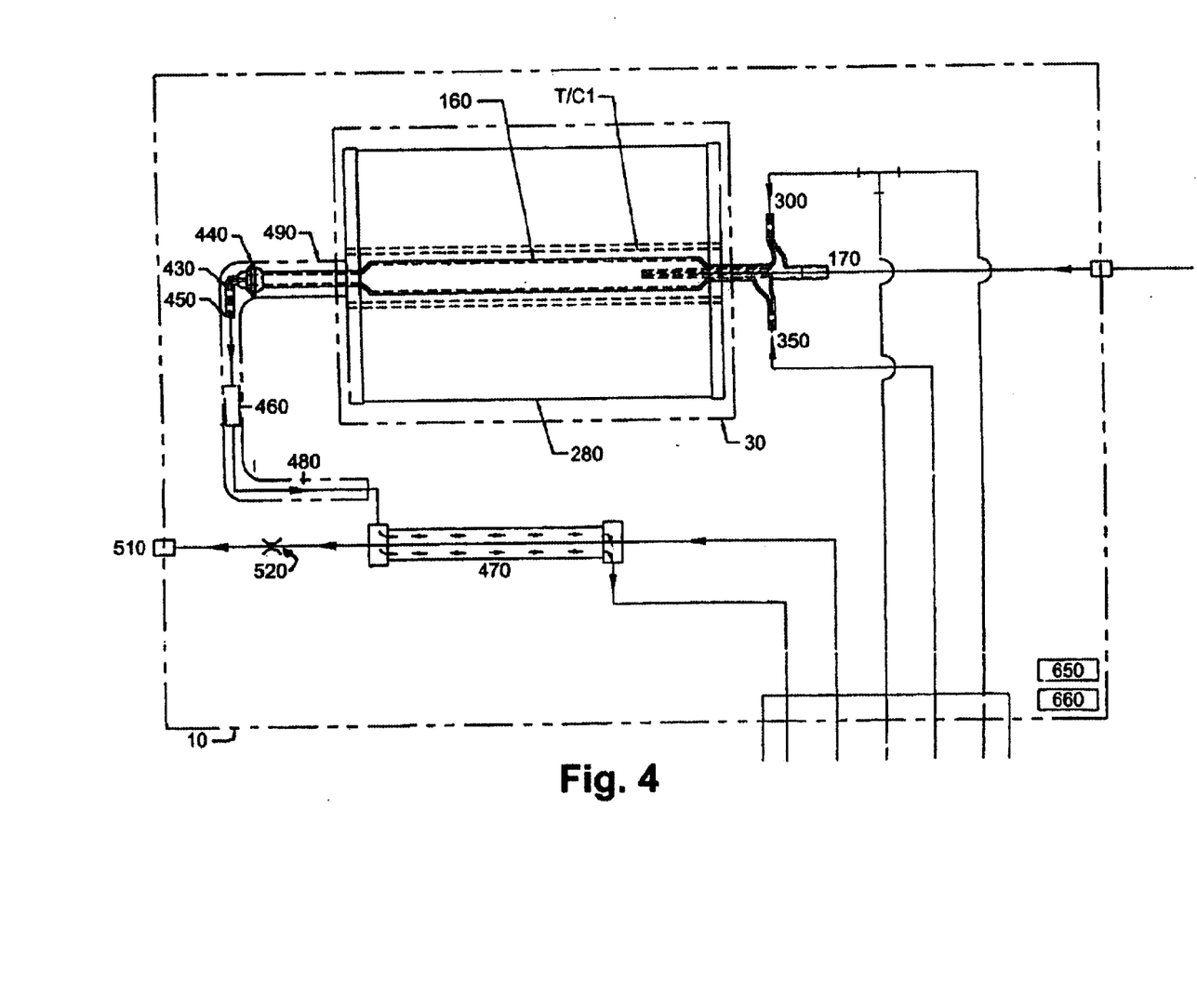
FIG. 4 is a section, to a larger scale, of Enclosure 1.

The instrument enclosures, 10 and 20 are preferably fitted with a standard air or inert gas purge, 640, to qualify for explosion proof certification. The purge gas is sent to both enclosures (purge plumbing connections not shown). The presence of combustible vapors at or above the Lower Explosive Limit is sensed by, 650, in enclosure, 10, and the signal sent to the PLC, 80, which alarms if vapors are detected. The temperatures of both enclosures are measured by thermocouples, 660, whose signals are monitored by the PLC, 80, which will alarm if the temperature falls outside the preset limits. Another safety feature is as follows. The pyrolysis furnace is enclosed in a sealed metal container, 30, whose outside surface temperature preferably does not exceed 200° C., the "maximum surface temperature classification", T3, defined for hazardous locations and relevant to our application. An apparatus located in a hazardous location should be classified according to the maximum surface temperature that can be generated by the instrument either in normal operation of fault condition. This maximum surface temperature should be lower that the ignition temperature of the gas present. The ignition temperatures of gasoline, diesel fuel and kerosene, among the possible samples for analysis under the present invention, are given as 250°, 330° and 210°–350° C., respectively. Depending on whether the European or North American standards apply, the maximum surface temperature is divided into 6 or 4 classifications, respectively. In both cases, the relevant classification here is T3, 200° C. The reason for this is if the enclosure, 10, purge fails and the electrical power is consequently cut off, the furnace will still be at a temperature over 1000° C. and may take hours to cool down. In use, the electrically heated center tube of the tube furnace is at the set point temperature (1000° to 1200° C.). This tube furnace comprises a tube, surrounded by high temperature insulating fiber, all enclosed in a cylindrical steel can. The surface temperature of the curved part of the steel can is somewhat less than 50° C. The ends of the furnace, on axis, are typically not insulated, except for the presence of the pyrolysis tube and ceramic end caps to hold the pyrolysis tube clear of the inside surface of the heated tube. Quite a lot of heat escapes from the ends and the surface temperatures range from about 50° C., far from the axis, to about 180° C. very close to the axis. Of course, gases can easily penetrate the space between the pyrolysis tube and the furnace tube, which is at about 1000° to about 1200° C. and remains well above the ignition temperature of a combustible gas even when the electricity is turned off. A sealed box may prevent ingress of possibly explosive gases in the event of purge failure of the main instrument enclosure, when the electricity would be turned off but the furnace would still be hot. The furnace insulation as well as the air blanket between the furnace and the box keep the surface temperature of the box well below T3 classification. Also, the outer surface of the furnace and the inner surface of the container, 30, should preferably be highly polished to reduce their emissivity and so minimize heat transfer by radiation. In normal operation, the furnace and surface of the enclosed box are kept cool by air or inert purge gas. In the event of purge and power failure cooling may take place by passive means such as convection, conduction and radiation to the surroundings.

There are various methods for processing the detector output to give sulfur content, which will be familiar to anyone experienced in the technology. A typical method is described here. The output signal of the sensor/amplifier subassembly is a voltage assumed to be proportional to $SO_2$ concentration in the gas passing over the sensor, for a given concentration range, or proportional to NO concentration, if an NO sensor is used. The method to be described assumes the calibration is linear over the range between the upper and lower calibration limits, for example, 0 to 20 ppm or 20 to 40 ppm sulfur in diesel fuel. The sensor signal can be integrated over preset time intervals corresponding to pyrolysis events and also to intervals between pyrolysis events. The "gross signal" can be integrated (electrical circuitry is not shown in Flow Diagram) over a preset time interval corresponding to the sensor response to the pyrolysis event. The "background signal", defined as the output during some interval between pyrolysis events, may also be integrated and stored. After suitable normalization for possibly different integration intervals and optional averaging over a preselected number of pyrolysis events, the background signal is subtracted from the gross signal to give the "net signal". This integral, I, is converted to sulfur concentration, C, by the following equation.

$$C=aI+b$$

Where a and b are calibration constants:

$$a=(C_h-C_l)/(I_h-I_l)$$

$$b=C_h-aI_h$$

The calibration is valid only between the two concentrations $C_h$ and $C_l$, which are the sulfur contents of the high and low calibration samples, respectively, giving the net signals $I_h$ and $I_l$, respectively.

In certain circumstances conversion must be made between ppm by weight and pmm by volume. The sample is delivered for injection in aliquots of constant volume (the sample loop volume) If a weight/volume result is required (e.g., grams per liter or grams per gallon) standards are quoted in terms of the same units of wt/vol, no density correction between standards and unknowns is needed. However, if a wt/wt result is required (e.g., g/g) and the standards are quoted in terms of wt/wt, a density correction must be made to both standards and unknowns:

$$(gS/g)_{unk} = (\text{density of std/density of unknown}) \times (gS/g)_{std}$$

If a wt/vol result is required and the standards are quoted in terms of wt/wt, only the standards need to be corrected for density:

$$(gS/ml)_{unk} = (\text{density of std, g/ml}) \times (gS/g)_{std}$$

If a wt/wt result is required and the standards are quoted in term of wt/vol, only the unknowns need to be corrected for their density:

$$(gS/g)_{unk} = (1/\text{density of unknowns}) \times (g/ml)_{std}$$

EXAMPLE

An especially preferred embodiment involves making available process fluid or calibration fluid at input port (port 1) of rotary valve, 40, and initiating rotary valve flush (loop recharge) cycle to charge the constant volume sample loop, 120. Fluid will flow through and out of port 6, keeping the constant volume sample loop, 120, full. At the same time the inert gas injection gas from micro-metering valve, 150, will be flowing through ports 4 and 5 of rotary valve, 40, and out through the injector, ensuring it is clear of previous sample. Change rotary valve, 40, to inject cycle. Injection gas will now push the fixed volume of process fluid out from the constant volume sample loop, 120, (in the reverse direction of charging) through the injector tube, 540, and into the pyrolysis tube through fitting, 170. Just before exiting the injector into the pyrolysis tube the sample will vaporize. Meanwhile the process (or calibration) fluid will be circulating into port 1 and out of port 2 of rotary valve, 40. The vaporized sample fluid first mixes with the carrier gas coming in at fitting, 300. The mixture exits the inner part of the pyrolysis tube into the main region where it is mixed with the pyrolysis gas coming in at fitting, 350. Thermal oxidation occurs in the main region of the pyrolysis tube which is at a temperature of about 1050° C. The hot gas mixture cools as it exits the pyrolysis tube through the elbow, 430, but is kept above its dew point by the heat tracing, if heat tracing is necessary, until the gas mixture reaches the dryer, 470, which reduces the relative humidity to about 50%, or between about 20 and 80%. Note that if no process or calibration fluid is being pyrolyzed, the relative humidity will soon drop to below 15% because the carrier and pyrolysis gases are dry. The sample gas passes through solenoid valves, 600, and thence though the humidifier, 590. The purpose of humidifier, 590, is to add humidity to the gas stream if the gas stream gets too dry. It works like a dryer in reverse. Liquid water in the annular space surrounding the membrane inner tube permeates through the tube wall only as long as there is a water vapor pressure gradient, which occurs when the sample gas relative humidity is below about 50%. Once the sample gas relative humidity reaches about 75% equilibrium conditions are achieved and water vapor permeation stops. The sample gas passes through the electrochemical cell assembly, 560 and/or 570 where the concentration of $SO_2$ is measured. The gas then passes through the relative humidity sensor, 610, then through the flow meter, 620, and finally through the scrubber cartridge, 630, containing granules of scrubber material, which remove any $SO_2$ before discharging to atmosphere. The $SO_2$ detector output is integrated over a time corresponding to the sample injection/pyrolysis interval. The sulfur content of the fluid sample is calculated by comparing the integrated output with those from calibration fluids treated the same way as the unknown. Calibration gas from the CAL GAS cylinder (optional) can be directed through detector, 560 and/or 570, by switching solenoid valves, 600. This bypasses the pyrolysis and is an independent check on detector, 560 and/or 570. It should not be confused with calibration proper, which employs calibration fluids, from the calibration fluid reservoir, 60, that are treated the same way as process fluids.

What is claimed is:

1. An on-stream analyzer for measuring the concentration of a substance in a fluid sample, said analyzer comprising:
    a. a sample injector for injecting a sample at a preset and controlled rate, the sample injector further comprising a pressure regulator coupled to a flow restrictor to control the rate of sample flow;
    b. a port for a carrier gas and a port for a pyrolysis gas;
    c. a thermal oxidizer comprising a tube furnace and a pyrolysis tube, connected to the sample injector;
    d. a sample conditioner, connected to and located downstream from the thermal oxidizer, said sample conditioner comprising a dryer wherein said dryer further comprises two concentric tubes, an inner tube composed of a membrane for transferring water vapor and an outer tube composed of inert material, wherein the dryer is configured such that during use a dry purge gas is in fluid communication with the inner tube and a sample gas is in fluid communication with the annular space between the inner and outer tube, and further wherein the inner tube is connected to an orifice to maintain positive pressure;
    e. a detector, connected to the sample conditioner, to measure the concentration of oxidized substance contained within the sample gas; and
    f. a programmable logic controller, connected to the detector, to calculate the concentration of oxidized substance contained within the gas mixture and consequently the concentration of substance in the original fluid sample.

2. The analyzer of claim 1 further wherein the flow restrictor is a metering valve.

3. The analyzer of claim 1 wherein the flow restrictor is a length of capillary tubing having a diameter of from about 0.001 to about 0.020 inches.

4. The analyzer of claim 3 wherein the capillary tubing has a diameter of about 0.004 inches.

5. The analyzer of claim 1 further comprising a container to enclose the thermal oxidizer.

6. The analyzer of claim 5 wherein, during operation of the analyzer, an outer surface temperature of the container does not exceed the lower explosive temperature of the sample being analyzed and the container prevents ingress of vapors of the sample being analyzed.

7. The analyzer of claim 1 wherein the carrier gas comprises argon, helium, mixtures thereof or mixtures of argon or helium with oxygen.

8. The analyzer of claim 1 wherein the pyrolysis gas comprises oxygen.

9. The analyzer of claim 1 further comprising one or more electronic flowmeters to measure the flow rates of carrier and pyrolysis gases introduced, and the total flow rate of the gas mixture.

10. The analyzer of claim 9, further comprising metering valves for controlling the flow rates of the carrier and pyrolysis gases.

11. The analyzer of claim 9 wherein the electronic flowmeters are connected to the programmable logic controller.

12. The analyzer of claim 9 wherein the electronic flowmeter further comprises a gas flow alarm to indicate a flow rate of carrier gas, pyrolysis gas, or gas mixture that falls outside a preselected range.

13. The analyzer of claim 1 wherein the tube furnace produces a temperature range of from about 1000° C. to about 1200° C.

14. The analyzer of claim 1 wherein the tube furnace produces a temperature of about 1050° C.

15. The analyzer of claim 1 wherein the detector comprises an assembly having one or more electrochemical cells.

16. The analyzer of claim 15 wherein one or more electrochemical cells measures the concentration of $SO_2$ in the mixture.

17. The analyzer of claim 15 wherein one or more electrochemical cells measures the concentration of NO in the mixture.

18. The analyzer of claim 15 wherein the one or more electrochemical cells further comprises an electrochemical cell capable of detecting $SO_2$ and an electrochemical cell capable of detecting NO.

19. The analyzer of claim 1 further comprising a combustible gas sensor to indicate the presence of combustible gas vapors.

20. The analyzer of claim 1 further comprising a humidifier located upstream from the assembly having one or more electrochemical cells.

21. The analyzer of claim 20 wherein the humidifier operates to maintain a relative humidity level of about 15 to 90%.

22. The analyzer of claim 20 wherein the humidifier comprises an alarm to indicate a relative humidity level which falls outside a preselected range.

23. The analyzer of claim 1 wherein the fluid sample is routed to the thermal oxidizer via the injector by non-electrical valves.

24. The analyzer of claim 23 wherein the non-electrical valves are pneumatically operated.

25. The analyzer of claim 1 wherein the sample conditioner further comprises a filter, and a heat trace element, the heat trace element further comprising self-limiting electrical heating wires effective to maintain the gas stream temperature above its dewpoint from the pyrolysis tube to the dryer.

26. The sample conditioner of claim 25 wherein the filter is a chemically inert membrane designed to prevent solid particles or liquid drops from passing downstream without significantly restricting the gas flow.

27. The analyzer of claim 1, further comprising a fluid sample outlet stream and a non-electric flow indicator to indicate the flow rate of the fluid sample outlet stream.

28. The analyzer of claim 1, further comprising a means for introducing one or more calibration fluids, contained in one or more calibration sample reservoirs, to the injector employing gas pressure and pneumatically operated valves.

29. The analyzer of claim 28, further comprising one or more metering valves to control the flow rate of the calibration fluids.

30. The analyzer of claim 1, further comprising solenoid valves controlled by the programmable logic controller to effectuate flow of a calibration gas directly to the detector, bypassing the thermal oxidizer and sample conditioner.

31. The analyzer of claim 1, further comprising solenoid valves and pneumatically-actuated pressure switches to send signals via solenoid valves to the programmable logic controller to indicate low gas pressure.

32. The analyzer of claim 1 wherein the inert material is a fluoropolymer or stainless steel.

33. The analyzer of claim 1 wherein the membrane is a membrane having sulfonic acid groups.

34. The analyzer of claim 1 wherein the orifice has a diameter of about 0.001 to about 0.05 inches.

35. The analyzer of claim 34 wherein the orifice has a diameter of about 0.0122 inches.

36. The analyzer of claim 34 wherein the electronic flow meter further comprises an alarm to indicate a purge gas flow that falls outside a preselected range.

37. The analyzer of claim 1 further comprising a metering valve to control the purge gas flow.

38. The analyzer of claim 37 further comprising an electronic flow meter, connected to the programmable logic controller, to monitor the purge gas flow.

39. An on-stream analyzer for detecting a substance in a fluid sample, said analyzer comprising:
 a. a fluid sample injector for injecting a sample at a preset and controlled rate;
 b. a thermal oxidizer, connected to the sample injector, to inject the sample into the thermal oxidizer and means to introduce a carrier gas and a pyrolysis gas to the sample under oxidation conditions;
 c. a sample conditioner, connected to the thermal oxidizer, to control the conditions of a resulting mixture, wherein the conditioner further comprises a dryer for removing water vapor, wherein the dryer further comprises two concentric tubes, an inner tube composed of a membrane for transferring water vapor and an outer tube composed of an inert material, wherein the dryer is configured such that a dry purge gas is in fluid communication with the inner tube and the sample gas is in fluid communication with the annular space between the inner and outer tube, and further wherein the inner tube is connected to an orifice to maintain positive pressure;
 d. one or more electrochemical cells, connected to the sample conditioner, to measure the concentration of a substance contained within the sample; and
 e. a programmable logic controller, connected to the electrochemical cells, to calculate the concentration of a substance contained within the mixture.

40. The analyzer of claim 39 wherein the sample injector further comprises a pressure regulator coupled to a metering valve to control the rate of sample flow.

41. The analyzer of claim 39 wherein the sample injector further comprises a pressure regulator coupled to a length of capillary tubing having a diameter of from about 0.0001 to about 0.020 inches to control the rate of sample flow.

42. The analyzer of claim 39 wherein the inert material is a fluoropolymer or stainless steel.

43. The analyzer of claim 39 wherein the membrane is a membrane having sulfonic acid groups.

44. An on-stream analyzer for detecting a substance in a liquid sample, said analyzer comprising:
 a. a liquid sample injector for injecting a sample at a preset and controlled rate, wherein the sample injector further comprises a pressure regulator coupled to a metering valve to control the rate of sample flow;
b. a combustible gas sensor to detect the presence of combustible gas vapors;
c. a thermal oxidizer comprising a tube furnace and a pyrolysis tube, connected to the sample injector and enclosed within a container;
d. a port for a carrier gas and a port for a pyrolysis gas;
e. a sample conditioner, connected to the thermal oxidizer, to control the conditions of a resulting mixture, wherein the conditioner further comprises:
   a dryer for removing water vapor, wherein the dryer comprises two concentric tubes, an inner tube composed of a perfluorinated membrane having sulfonic acid groups and an outer tube composed of a fluoropolymer, wherein the dryer is configured such that a dry purge gas is in fluid communication with the inner tube and the sample gas is in fluid communication with the annular space between the inner and outer tube, and further wherein the inner tube is connected to an orifice to maintain positive pressure;
   a heat trace element comprising self-limiting electrical heating wires effective to maintain the gas stream temperature above its dewpoint from the pyrolysis tube to the dryer;
   a humidifier that operates to maintain a relative humidity level of the gas stream from about 15 to about 90%, the humidifier further comprising an alarm to indicate a humidity level which falls outside the preselected humidity level;
f. one or more electrochemical cells, connected to the sample conditioner, to measure the concentration of a substance contained within the sample;
g. one or more pneumatic valves for introducing calibration samples and one or more calibration sample reservoirs;
h. one or more solenoid valves, connected to the programmable logic controller, to effectuate flow of one or more calibration gases directly to the detector, bypassing the thermal oxidizer and sample conditioner;
i. one or more pneumatically operated valves to effectuate the routing of the liquid and calibration samples; and
j. a programmable logic controller, connected to the electrochemical cell, to calculate the concentration of pollutants contained within the mixture.

* * * * *

UNITED STATES PATENT AND TRADEMARK OFFICE
CERTIFICATE OF CORRECTION

PATENT NO. : 6,830,730 B2
DATED : December 14, 2004
INVENTOR(S) : John R. Rhodes It is certified that error appears in the above-identified patent and that said Letters Patent is hereby corrected as shown below:

Title page,
Item [73], Assignee, delete "SpectrolAnalytical" please insert -- Spectro Analytical --.
Item [56], References Cited, OTHER PUBLICATIONS,
"Schwarz, et al." reference, delete "dulfur fioxide" and insert -- sulfur dioxide --.

Column 4,
Line 48, delete "filling" please insert -- falling --.

Column 7,
Line 40, delete "1" please insert -- 4 --.
Line 65, delete both occurrences of "car" please insert -- cal --.

Column 13,
Line 13, delete "$s_{td}$" please insert -- $_{std}$ --.
Line 25, delete "$(gS/g)_{unk}=(1/\text{density of unknowns})\times(g/ml)_{std}$" please insert -- $(gS/g)_{unk}=(1/\text{density of unknowns})\times(gS/ml)_{unk}$ --.

Signed and Sealed this

Twenty-ninth Day of March, 2005

JON W. DUDAS
*Director of the United States Patent and Trademark Office*